US006424869B1

(12) United States Patent
Carr et al.

(10) Patent No.: US 6,424,869 B1
(45) Date of Patent: Jul. 23, 2002

(54) DUAL MODE TRANSURETHRAL MICROWAVE WARMING APPARATUS

(75) Inventors: Kenneth L. Carr, Harvard; James F. Regan, Waltham, both of MA (US)

(73) Assignee: Meridian Medical Systems, LLC, Ayer, MA (US)

( * ) Notice: Subject to any disclaimer, the term of this patent is extended or adjusted under 35 U.S.C. 154(b) by 0 days.

(21) Appl. No.: 09/476,201

(22) Filed: Jan. 3, 2000

Related U.S. Application Data

(63) Continuation-in-part of application No. 09/368,179, filed on Aug. 4, 1999, now Pat. No. 6,210,367, which is a continuation-in-part of application No. 08/977,747, filed on Nov. 25, 1997, now Pat. No. 6,146,359, which is a continuation-in-part of application No. 08/524,392, filed on Sep. 6, 1995, now Pat. No. 5,690,614.

(51) Int. Cl.$^7$ .................................................. A61N 5/02
(52) U.S. Cl. ...................... 607/101; 607/102; 607/113; 607/156
(58) Field of Search ............................ 604/113–114, 22; 128/736; 607/101, 156, 102, 113; 606/27–31

(56) References Cited

U.S. PATENT DOCUMENTS

| | | | | |
|---|---|---|---|---|
| 4,346,716 A | * | 8/1982 | Carr | 128/653 |
| 4,557,272 A | * | 12/1985 | Carr | 128/736 |
| 4,583,556 A | * | 4/1986 | Hines et al. | 128/804 |
| 4,614,514 A | * | 9/1986 | Carr et al. | 604/113 |
| 4,825,880 A | * | 5/1989 | Stauffer et al. | |
| 4,945,912 A | * | 8/1990 | Langberg | 128/642 |
| 4,967,765 A | * | 11/1990 | Turner et al. | |
| 5,073,167 A | * | 12/1991 | Carr et al. | 604/114 |
| RE33,791 E | * | 1/1992 | Carr | 374/122 |
| 5,234,004 A | * | 8/1993 | Hascoet et al. | 607/116 |
| 5,344,435 A | * | 9/1994 | Turner et al. | |
| 5,364,336 A | * | 11/1994 | Carr | 600/2 |
| 5,562,641 A | * | 10/1996 | Flomenblit et al. | |
| 5,683,382 A | * | 11/1997 | Lenihan et al. | |
| 5,987,360 A | * | 11/1999 | McGrath et al. | |

* cited by examiner

*Primary Examiner*—Mark Bockelman
(74) *Attorney, Agent, or Firm*—Cesari and McKenna, LLP

(57) ABSTRACT

A dual mode transurethral warming apparatus particularly adapted to treat benign prostatic hyperplasia includes a urethral catheter dimensioned for insertia through the urethra. The catheter includes an elongated flexible tube having a plurality of longitudinal lumens extending between the ends of the tube. A coaxial cable extends along one of the lumens to an antenna in the form of a multi-turn helical winding wound around the outside of the tube. A first connector connects one of the cable conductors to one end of the winding and a second connector connects the other cable conductor to the other end of the winding so that the antenna formed by the winding is larger in diameter than the cable, and all of the lumens are located within the winding. The cable is connected to a control and display unit which includes a transmitter which provides electromagnetic energy via the cable to the antenna so that the antenna generates an electromagnetic field sufficient to treat tissue adjacent the antenna. The same antenna also detects thermal energy emitted by the tissue thereby developing an electrical signal which is fed via the cable to a receiver in the form of a radiometer in the control and display unit. The cable is connected to the transmitter and receiver by way of a diplexer which separates the transmitter and receiver signal frequencies allowing the use of the common coaxial cable and antenna for both heating the tissue and sensing the actual temperature of the tissue. Preferably, the catheter includes an inflatable balloon at the distal end of the tube, the balloon being inflated by flowing an inflation fluid to the balloon via one of the lumens in the tube. Other working lumens may be included in the tube for providing drainage and for coolant circulation to cool the exterior surfaces of the catheter.

12 Claims, 3 Drawing Sheets

DUAL MODE TRANSURETHRAL MICROWAVE WARMING APPARATUS

RELATED APPLICATION

This application is a continuation-in-part of Ser. No. 09/368,179 filed Aug. 4, 1999, now U.S. Pat. No. 6,210,367, which is a continuation-in-part of Ser. No. 08/977,747, filed Nov. 25, 1997, now U.S. Pat. No. 6,146,359, which is a continuation-in-part of Ser. No. 08/524,392, filed Sep. 6, 1995, now U.S. Pat. No. 5,690,614.

BACKGROUND OF THE INVENTION

This application relates to transurethral hypothermia apparatus. It relates more particularly to a dual mode (i.e heating and sensing) transurethral microwave warming apparatus.

It is well known that heat can be used to reduce an enlarged prostate. Benign prostatic hyperplasia (BPH) is a common disease among aging men that may lead to several complications such as urinary tract infection, acute urinary retention or uremia. In the U.S. alone, there are approximately 400,000 transurethral resection procedures performed each year involving general anesthesia and hospitalization to treat the above problem. Many patients are poor surgical risks due to age and possible co-existing health problems.

Microwave hyperthermia appears to be a practical alternative to transurethral resection for the prostate, the usual surgical procedure. Microwave transurethral hyperthermia involves insertion of a small catheter, including a microwave antenna, into the bladder via the urethra. This procedure can be performed in an outpatient basis without the need for general anesthesia.

It is also well known that hyperthermia can be used as an adjunct to ionizing radiation as a treatment for a malignant disease. According to the American Cancer Society, cancer of the prostate is currently the second most lethal cancer in American men. Numerous studies have demonstrated that microwave hyperthermia can be a valuable adjunct to radiation therapy in the treatment of prostrate cancer. The combination of microwave heating and ionizing radiation is far more effective than either of the treatments alone, thereby significantly reducing the level of ionizing radiation required. However, the success of hypothermia rests on the ability to effectively heat the tumor volume to therapeutic temperatures without causing damage to the adjacent normal tissue.

Conventional transurethral catheters used in prostrate applications have multiple lumens with at least one lumen dedicated to the microwave antenna or applicator. The catheter also has other working lumens used for coolant, drainage, temperature probes and inflation fluid, e.g. air, for inflating a balloon at the tip of the catheter for positioning the catheter after insertion.

FIG. 5 of the drawings shows a conventional transurethral catheter used in prostate applications. It includes an elongated probe or body 10 having a plurality of length-wise lumens. There is a central lumen 12 with a counterbore 12*a* for accommodating a coaxial cable 14. The cable's center conductor extends to the distal end of lumen 12 and constitutes an antenna 16. Probe 10 also has a second, generally U-shaped lumen 18 whose legs 18*a* are located radially outboard lumen 12 and which provides a path for the circulation of a coolant fluid through the probe to cool the external surfaces of the probe. As noted previously, catheters of this type usually include a balloon 22 adjacent to the distal end of probe 10. Therefore, an additional lumen 24 extends along probe 10 to carry the inflation fluid to the balloon. Various other working lumens may extend along probe 10. For example, there may be a lumen 25 which runs the length of the probe and is used for the drainage of body fluids after the catheter is inserted in a patient. There may also be a lumen indicated at 26 for accommodating one or more heat sensors 30 such as a thermocouple, thermister or fiberoptic device. All of the working lumens extend to the proximal end of the probe 10 where they connect to tubes which lead to various units supporting the above-described functions of the lumens. The FIG. 5 catheter is fully described in U.S. Pat. No. 5,234,004.

As seen from the above patent, with the balloon 22 in its deflated condition shown in solid lines in FIG. 5, the distal end 10*a* of the probe 10 may be inserted into the urethra up to the level of the tissue to be treated by the thermal affect at which level the balloon 22 reaches the patient's bladder. Thus, after inflating the balloon by flowing an inflation fluid such as air through lumen 24 so that the balloon expands as shown in phantom in FIG. 5, the catheter is locked in the bladder neck thereby achieving a precise positioning of antenna 16 relative to the patient's prostate which surrounds the urethra, that position being maintained during the entire treatment.

After probe 10 has been positioned thusly, microwave power may be delivered via cable 14 to antenna 16 which produces a radiation pattern that heats the tissue near the probe. Preferably, a coolant is circulated through lumen 18 in order to lower the surface temperature of probe 10 to prevent overheating the tissue right next to the probe. As described in the above patent, a heat sensor 30 may be present in lumen 26 for sensing the temperature on or inside probe 10. The output from the sensor can then be used to control the power delivered to antenna 16 so that the tissue to be subjected to the thermal effect is heated to within a selected temperature range.

Transurethral catheters of the above type are disadvantaged in that the fluid-carrying lumens 18, 24 and 25 are located between antenna 16 and the tissue surrounding probe 10. Resultantly, the various fluids flowing through those lumens perturb the antenna pattern and absorb microwave energy. The same is true with the temperature sensor(s) 30 in lumen 26. The result is that the catheter may heat the adjacent tissue unevenly so that some tissue is heated excessively while other tissue is not heated enough to achieve the desired thermal effect. This problem is exacerbated by the fact that the temperature sensor(s) 30 measure the temperature on or in probe 10, not the actual temperature of the tissue surrounding the probe. The upshot is that prior catheters of this type do not achieve the desired degree of temperature control of the tissue being heated.

The conventional catheters suffer also because of the presence of temperature sensing devices in the catheters. More particularly, thermisters and thermocouples require connecting wires which are prone to failure. They also reduce the catheter's flexibility making it more difficult to thread the catheter through the urethra. On the other hand, fiberoptic sensors are fragile and quite expensive thereby increasing the overall cost of the apparatus.

Accordingly, it is an object of the present invention to provide improved transurethral microwave warming apparatus particularly adapted to treat benign prosthetic hyperplasia.

Another object of the invention is to provide such apparatus which includes a catheter able to heat the tissue to be treated relatively uniformly.

Another object of the invention is to provide apparatus of this type which can precisely monitor the actual temperature of the tissue being treated.

A further object of the invention is to provide transurethral microwave warming apparatus which accurately monitors tissue temperature without the need for thermocouples, fiberoptic circuitry or other temperature sensing hardware in the apparatus' catheter or probe.

Yet another object of the invention is to provide a transurethral microwave catheter which is quite flexible to facilitate passage through the urethra.

A further object of the invention is to provide such a catheter which is relatively inexpensive to manufacture in quantity.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

SUMMARY OF THE INVENTION

Our dual mode transurethral warming apparatus includes a urethral catheter dimensioned for insertia through the urethra. The catheter includes an elongated flexible tube having a plurality of longitudinal lumens extending between the ends of the tube. A coaxial cable extends along one of the lumens to an antenna in the form of a multiturn helical winding wound around the outside of the tube. A first connector connects one of the cable conductors to one end of the winding and a second connector connects the other cable conductor to the other end of the winding so that the antenna formed by the winding is larger in diameter than the cable and all of the lumens are located within the winding.

The cable is connected to a control and display unit which includes a transmitter providing electromagnetic energy via the cable to the antenna so that the antenna generates an electromagnetic field sufficient to treat tissue adjacent to the antenna. The same antenna also detects thermal energy emitted by the tissue thereby developing an electrical signal which is fed via the cable to a receiver in the form of a radiometer in the control and display unit. As will be described in detail later, the cable is connected to the transmitter and receiver by way of a diplexer which separates the transmitter and receiver signal frequencies allowing the use of the common coaxial cable and antenna for both heating the tissue and sensing the actual temperature of the tissue.

Preferably, the catheter includes an inflatable balloon at the distal end of the tube, the balloon being inflated by flowing a gas or liquid inflation fluid to the balloon via one of the lumens in the tube. Other working lumens may be included in the tube for providing drainage and/or for coolant circulation to cool the exterior surfaces of the catheter.

BRIEF DESCRIPTION OF THE DRAWINGS

For a further understanding of the nature and objects of the invention, reference should be made to the following detailed description taken in connection with the accompanying drawings, in which.

DETAILED DESCRIPTION OF AN ILLUSTRATIVE EMBODIMENT

Figure 1:
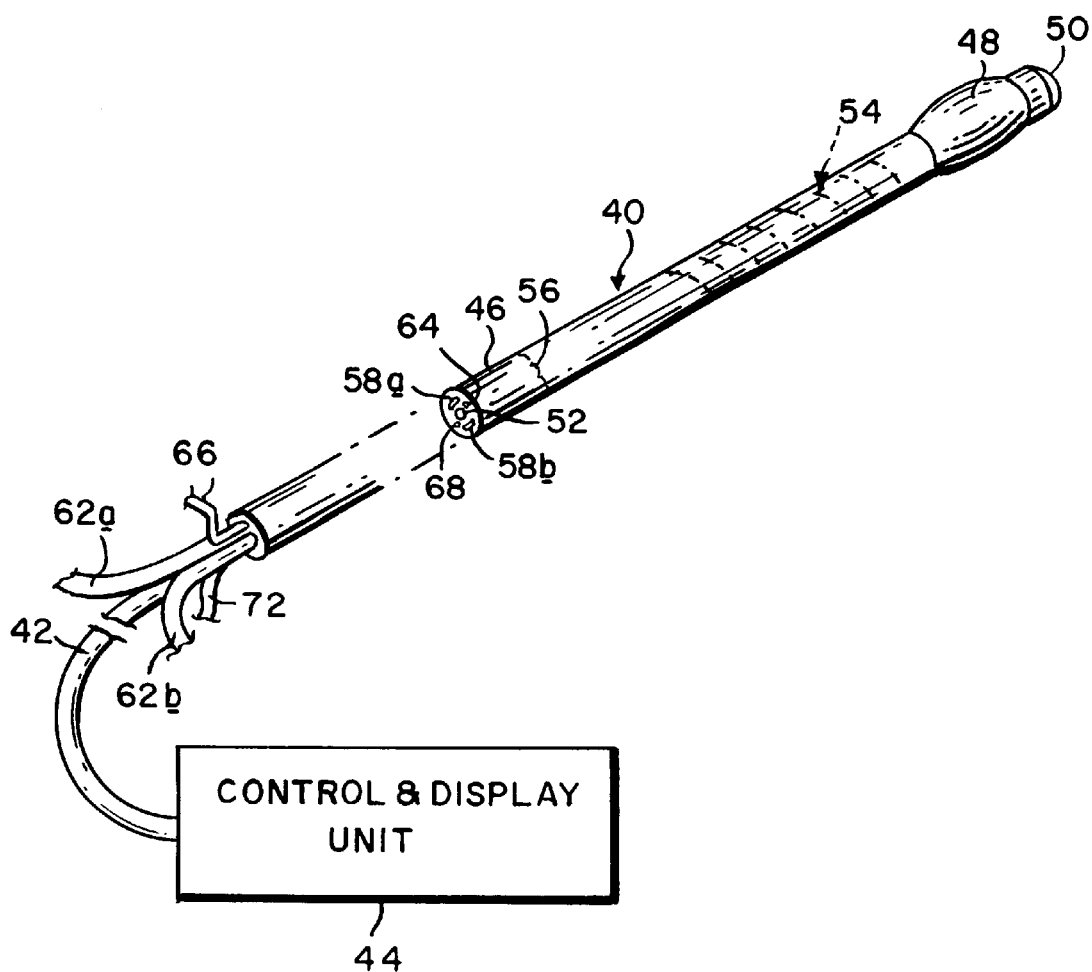
FIG. 1 is an isometric view with parts broken away of a catheter for transurethral microwave warming apparatus according to the invention.
Figure 2:
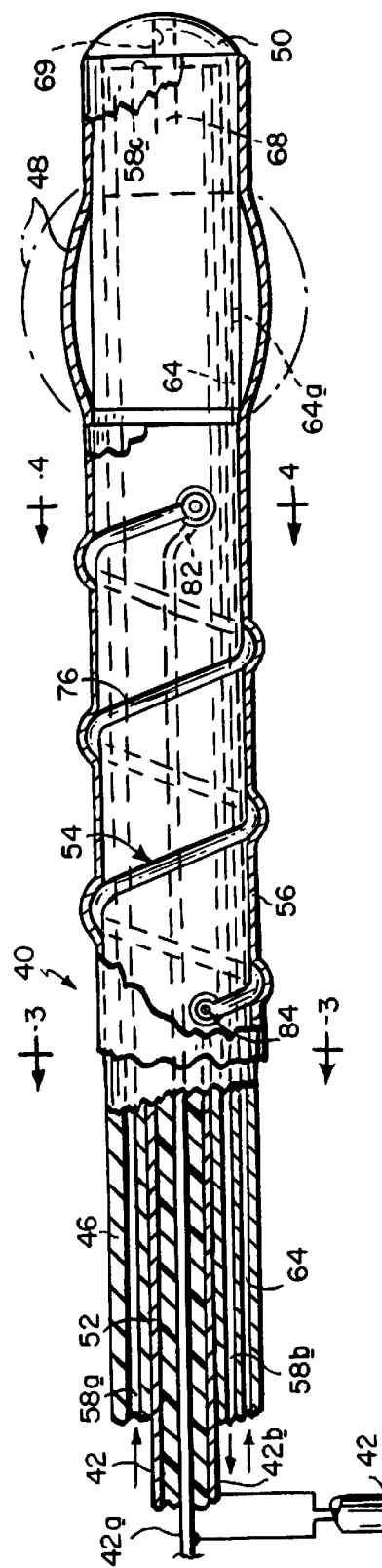
FIG. 2 is a diagrammatic view with parts in section of transurethral microwave warming apparatus incorporating the FIG. 1 catheter.
Figure 2:
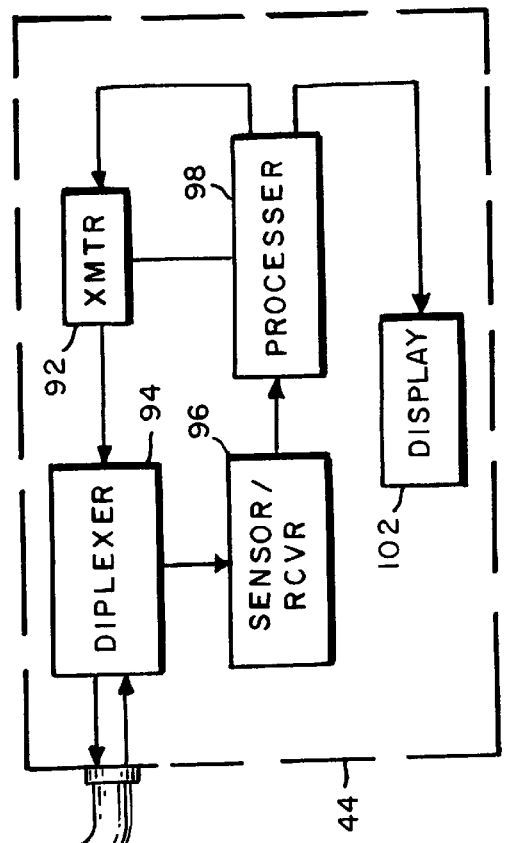

Referring to FIGS. 1 and 2 of the drawings, my transurethral microwave warming apparatus comprises a catheter shown generally at 40 connected by means of a coaxial cable 42 to a control and display unit 44. Catheter 40 consists of a relatively long, small diameter flexible tube 46 made of a biocompatible material such as medical grade silicone. An annular balloon 48 is located adjacent to the distal end of tube 46. Also, the tube is formed with a plurality of longitudinal lumens all of which may extend the full length of the tube. The distal ends of selected lumens may be closed by a cap 50 sealed to the distal end of tube 46. In the illustrated probe, there is an axial lumen 52 accommodating the coaxial cable 42 which delivers power to a helical microwave antenna 54 wound around tube 46 just behind balloon 48. Preferably, the antenna (and perhaps the rest of tube 46) is covered by a covering 56 such as a thin protective coating or sleeve of a suitable insulating material such as Teflon brand shrink-tubing.

Tube 46 also has a pair of working lumens 58a and 58b whose distal ends are interconnected by a lateral slot 58c (FIG. 2) formed in the distal end of tube 46 and covered by cap 50 for circulating a coolant through the catheter to cool the external surfaces of the catheter. The proximal ends of lumens 58a and 58b are as connected to tubes 62a and 62b respectively, which lead to a coolant source (not shown) and a drain (not shown). There is also a lumen 64 having a side branch 64a, (FIG. 2), i.e., a lateral hole in tube 46, which communicates with the interior of balloon 48. The proximal end of lumen 64 is connected to a tube 66 leading to an inflation fluid source (not shown). Finally, tube 46 may contain a longitudinal drainage lumen 68 which is aligned with a hole 69 in cap 50 as shown in FIG. 2. The proximal end of lumen 68 is connected to a tube 72 leading to a conventional aspirator or vacuum drain (not shown).

Figure 3:
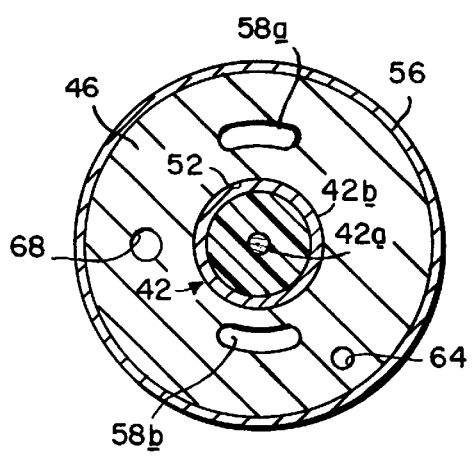
FIG. 3 is a sectional view taken along line 3—3 of FIG. 2.
Figure 4:
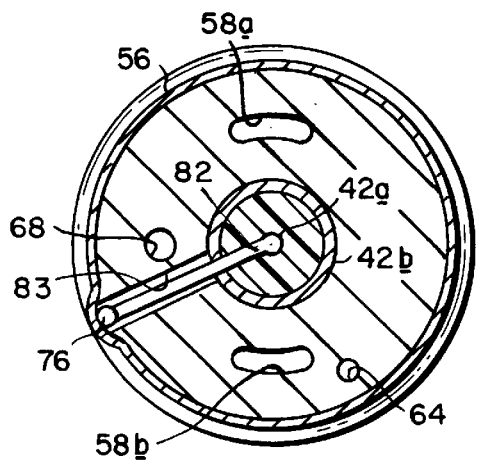
FIG. 4 is a similar view taken along line 4—4 of FIG. 2.

Referring now to FIGS. 2 to 4, antenna 54 comprises a helical winding 76 on tube 46 just behind balloon 48. For case of illustration, we have shown a winding with only a few turns; in actuality, the winding may have many, more closely spaced turns. In any event, the inner conductor 42a of cable 42 extends along tube lumen 52 to a point adjacent the distal end of winding 76 where the conductor 42a is connected to that winding end by a feed-through 82 extending through a radial hole 83 in tube 46 as best seen in FIG. 4. A similar feed through 84 connects the proximal end of winding 76 to the outer conductor 42b of cable 42.

As seen from the drawing figures, the covering 56 snugly encircles and covers antenna 54. Actually, balloon 48 and covering 56 may be constituted by a single length of elastic tubing which is sealed to tube 46 at the distal end segment of the tube and just beyond the end of antenna 54 to thereby define the confines of the balloon.

Referring to FIG. 2, as noted previously, the control and display unit 44 supplies microwave power to cable 42. Unit 44 is fully described in the above-identified related U.S. Pat. No. 5,690,614, whose contents are hereby incorporated by reference herein. Suffice it to say here that unit 44 includes a transmitter 92 which operates at a frequency of, say, 915 MHz ($F_T$). The output from the transmitter is coupled to coaxial cable 42 by way of a diplexer 94. The transmitted power causes antenna 54 to emit electromagnetic radiation. As the tissue surrounding catheter 40 absorbs energy, its temperature is elevated.

The same antenna also detects the thermal radiation emitted by the tissue and applies a corresponding electrical signal via diplexer 94 to a microwave sensor/receiver 96 in the form of a radiometer in control and display unit 44. Preferably, sensor/receiver 96 has a radiometer frequency appreciably different from that of transmitter 92, e.g., in the range of 3.7 to 4.2 $GH_Z$, with a center frequency of 4.0 $GH_Z$ ($F_R$). In some applications, the radiometer frequency may be lower than the heating frequency, e.g., $F_R$=1200 $MH_Z$; $F_T$=2400 $MH_Z$.

Due to the presence of diplexer 94, the receiver 96 detects only that energy associated with the tissue being heated. The temperature-indicating signal from receiver 96 may then be processed by a processor 98 in unit 44 to maintain the tissue at a selected temperature according to a selected temperature vs time profile programmed into processor 98.

Processor 98 also controls a display 102 in unit 44 which can display in real time the actual temperature of the tissue in the vicinity of catheter 40 and other useful information such as the selected temperature vs time profile, diagnostic data the like. The diplexer 94 shown in FIG. 2 separates the transmitter heating frequency $F_T$ from the receiver frequency $F_T$ allowing the use of the common coaxial cable 42 and the common antenna 54 in catheter 40, all is described in the above patent. Resultantly, the transmitter signal is not coupled to the receiver arm of the diplexer (and vice versa) thereby minimizing transmission losses.

The formation of antenna 54 as a winding on the outside of tube 46 produces several distinct advantages. First of all, the antenna 54 is larger in diameter than the coaxial cable 42 which feeds the antenna making the antenna more broadband. Secondly, all of the lumens constituting fluid pathways in the catheter are located inside the antenna winding 76 and not between the antenna and the tissue to be heated. Resultantly, the various fluids flowing through those lumens do not perturb the radiation pattern or field of the antenna. This construction also provides a more broadband match since the dielectric loading of the antenna (including the fluids) more closely matches the dielectric constant of the tissue adjacent catheter 40.

It is also important to note that the use of radiometric sensing of temperature allows the common antenna 54 to provide both heating of tissue and the measurement of actual tissue temperature. This eliminates the need in the catheter for fiberoptic circuitry or thermocouples with their associated wires, amplifiers, connectors, etc. The elimination of such temperature-sensing hardware improves system reliability and enhances the flexibility of catheter 40. In addition, it greatly simplifies the construction of, and therefore lowers the cost of, catheter 40.

In use, catheter 40 with balloon 48 deflated as shown in solid lines in FIG. 2 is threaded through the urethra until the balloon reaches the patient's bladder. Then, the balloon is inflated with a fluid such as air or saline solution so that it assumes the position shown in phantom in FIG. 2. This locks the catheter in the bladder neck so as to precisely position antenna 54 adjacent the prostate surrounding the urethra.

Then, while a coolant is circulated through the catheter via lumens 58a to 58c, unit 44 is activated so that antenna 54 transmits microwave energy in a selected radiation pattern. This energy is absorbed by the tissue adjacent to the antenna thereby heating that tissue. As noted previously, since all of the working lumens in the catheter are located radially inboard the antenna winding 76, those lumens and any fluids flowing therethrough have minimal effect on the radiation pattern emitted by antenna 54. Therefore, the antenna produces a uniform heating of the tissue adjacent the catheter.

Since the apparatus functions in a dual mode, the antenna 54 also detects the thermal radiation emitted by the tissue adjacent catheter 40 and provides temperature signals to the control and display unit 44 as described above, enabling that unit to closely control the power delivered to antenna 54 to maintain the tissue temperature within a selected temperature range for the necessary time period to accomplish the desired thermal effect.

Figure 5:
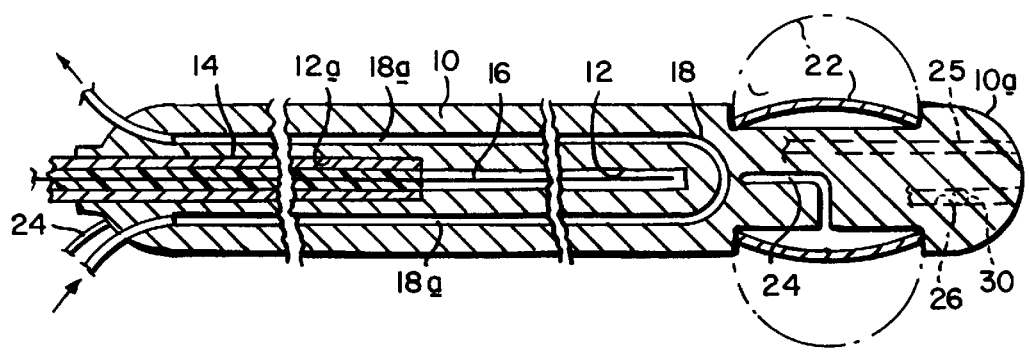
FIG. 5, already described, is a view similar to FIG. 2 showing a conventional transurethral microwave warming catheter.

Catheter 40 being formed as a simple tube with an outside winding as the antenna can be made relatively easily and, therefore, at minimum cost. This, coupled with the fact that the apparatus does not rely on thermocouples, fiberoptic circuitry and the like to monitor temperature, means that the overall apparatus can be made more easily and at less cost then prior such instruments typified by the one depicted in FIG. 5.

When the hypothermia procedure is completed, the coolant and unit 44 may be turned off and the balloon 48 deflated to its solid line condition shown in FIG. 2 by removing the inflation fluid, enabling the catheter 40 to be withdrawn from the patient's urethra.

It will thus be seen that the objects set forth above, among those made apparent from the preceding description, are efficiently attained. Also, certain changes may be made in the above construction without departing from the scope of the invention. For example, catheter 40 may include a second helical antenna in the form of a second winding on tube 46 coaxial to winding 76. This second winding may be serviced by a second coaxial cable extending from a control and display unit capable of transmitting to and receiving from both antennas together, or independently. This would give the apparatus a greater heating capability and flexibility. Also, the apparatus may be modified to utilize an RF transmitter to accomplish RF, instead of, microwave, heating of the tissue. Therefore, it is intended that all matter contained in the above description or shown in the accompanying drawing be interpreted as illustrative and not in a limiting sense.

It is also to be understood that that following claims are intended to cover all of the generic and specific features of the invention described herein.

What is claimed is:

1. Transurethral warning apparatus comprising
   a urethral catheter dimensioned for insertion through the urethra, said catheter including an elongated flexible tube having a proximal end, a distal end and a plurality of longitudinal lumens extending between said ends;
   a cable extending along one of said lumens, said cable having at least two conductors;
   an antenna in the form of a multi-turn helical winding wound around the outside of said tube, said winding having a proximal end and a distal end;
   a first electrical connection extending from one of the conductors through the tube to the proximal end of the winding;
   a second electrical connector extending from the other of said conductors through the tube to the distal end of the winding whereby said antenna is larger in diameter than said cable and all of said lumens are contained within said winding, and means for delivering electromagnetic energy to said cable so that the antenna generates an electromagnetic field sufficient to heat tissue in the vicinity of said antenna, said delivering means including a transmitter for transmitting a first signal of a first frequency capable of heating tissue;

a receiver for receiving a second signal of a second frequency indicative of thermal radiation, said receiver producing an output signal in response thereto, and a diplexer connecting the proximal end of the cable to the transmitter and receiver, said diplexer coupling said first signal from the transmitter only to said antenna while coupling said second signal from said antenna only to said receiver so that the apparatus can simultaneously heat tissue and determine the actual temperature of the tissue in the vicinity of said antenna.

2. The apparatus defined in claim 1 and further including an annular inflatable balloon encircling said tube between the winding and the distal end of the tube;

a side port in the tube having one end communicating with the interior of the balloon and a second end communicating with a second one of said plurality of lumens, and means for delivering an inflation fluid to said second lumen.

3. The apparatus defined in claim 2 and further including a sleeve snugly covering over said winding.

4. The apparatus defined in claim 3 wherein said balloon and sleeve are constituted by a single length of elastic tubing, and further including means for sealing the sleeve to the tube between the antenna and the side port and the between the side port and the distal end of the tube so as to define the confines of the balloon.

5. The apparatus defined in claim 2 wherein a third one of said plurality of said lumens extends the entire length of the catheter, and further including means for drawing a vacuum in said third lumen.

6. The apparatus defined in claim 1 and further including means for connecting a selected couple of said plurality of lumens, other than said one lumen, at the distal end of the tube to form a lumen loop in the tube, and means for circulating a coolant along said lumen loop.

7. The apparatus defined in claim 1 wherein said diplexer comprises a first arm connected between the transmitter and the antenna and containing a low-pass filter which passes only said first signal, and a second arm connected between the receiver and a junction between the low pass filter and the antenna, said second arm containing a band pass filter which passes said second signal but blocks said first signal.

8. The apparatus defined in claim 1 wherein the frequency of the second signal is much higher than the frequency of the first signal.

9. The apparatus defined in claim 8 wherein the receiver comprises a radiometer.

10. The apparatus defined in claim 9 wherein said catheter also includes expandable means located adjacent to said antenna, said expandable means being movable between a contracted position wherein the expandable means lies substantially within the cross sectional envelope of the catheter and an expanded position wherein the expandable means extend outside said envelope, and means in said tube for moving the expandable means between said positions.

11. The apparatus defined in claim 1 and further including a display responsive to said output signal for producing an indication of the actual temperature of the tissue.

12. The apparatus defined in claim 11 and further including control means responsive to said output signal for controlling the transmitter to heat tissue according to a selected temperature/time profile.

* * * * *